United States Patent
Brown et al.

(10) Patent No.: US 8,639,329 B2
(45) Date of Patent: Jan. 28, 2014

(54) CIRCUITS AND METHODS FOR ARTIFACT ELIMINATION

(75) Inventors: Edgar A. Brown, Decatur, GA (US); James D. Ross, Decatur, GA (US); Richard A. Blum, Atlanta, GA (US); Stephen P. DeWeerth, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 616 days.

(21) Appl. No.: 11/511,794

(22) Filed: Aug. 29, 2006

(65) Prior Publication Data

US 2007/0178579 A1 Aug. 2, 2007

Related U.S. Application Data

(60) Provisional application No. 60/712,651, filed on Aug. 30, 2005.

(51) Int. Cl.
*A61N 1/00* (2006.01)
*A61B 5/05* (2006.01)

(52) U.S. Cl.
USPC .......... 607/11; 607/2; 607/62; 600/544; 600/545; 600/546; 600/547; 600/554; 435/283.1; 435/286.1

(58) Field of Classification Search
USPC ........ 600/554, 544–547; 435/283.1, 286.1, 4; 607/2, 11, 62
See application file for complete search history.

(56) References Cited

U.S. PATENT DOCUMENTS

| | | | | |
|---|---|---|---|---|
| 3,885,552 A * | 5/1975 | Kennedy | .......................... | 607/27 |
| 4,537,196 A * | 8/1985 | Phillipps et al. | .............. | 600/300 |
| 4,821,724 A * | 4/1989 | Whigham et al. | .............. | 607/13 |
| 5,215,084 A * | 6/1993 | Schaldach | ........................ | 607/19 |
| 5,758,651 A * | 6/1998 | Nygard et al. | ................. | 600/554 |
| 6,114,164 A | 9/2000 | Dennis et al. | | |
| 7,089,049 B2 | 8/2006 | Kerver et al. | | |
| 7,277,758 B2 * | 10/2007 | DiLorenzo | ...................... | 607/45 |
| 7,317,948 B1 * | 1/2008 | King et al. | ....................... | 607/62 |
| 7,324,851 B1 * | 1/2008 | DiLorenzo | ...................... | 607/45 |
| 7,403,820 B2 * | 7/2008 | DiLorenzo | ...................... | 607/45 |
| 7,577,480 B2 * | 8/2009 | Zeijlemaker | .................... | 607/11 |
| 2005/0277844 A1 | 12/2005 | Strother et al. | | |
| 2005/0282149 A1 | 12/2005 | Kovacs et al. | | |

OTHER PUBLICATIONS

J. L. Novak et al., "Multisite hippocampal slice recording and stimulation using a 32 element microelectrode array," J. Neurosci. Meth., vol. 23, No. 2, pp. 239-247, Mar. 1988.

(Continued)

*Primary Examiner* — Sean Dougherty
(74) *Attorney, Agent, or Firm* — Jones Day

(57) ABSTRACT

Disclosed are apparatus and methods that provide the ability to electrical stimulate a physical system, and actively eliminate interference with signal acquisition (artifacts) that arises from the stimulation. The technique implemented in the circuits and methods for eliminating interference connects a discharge path to a physical interface to the system to remove charge that is built-up during stimulation. By placing the discharge path in a feedback loop that includes a recording preamplifier and AC-coupling circuitry, the physical interface is brought back to its pre-stimulation offset voltage. The disclosed apparatus and methods may be used with piezoelectric transducers, ultrasound devices, optical diodes, and polarizable and non-polarizable electrodes. The disclosed apparatus can be employed in implantable devices, in vitro or in vivo setups with vertebrate and invertebrate neural tissue, muscle fibers, pancreatic islet cells, osteoblasts, osteoclasts, bacteria, algae, fungi, protists, and plants.

21 Claims, 4 Drawing Sheets

(56) References Cited

OTHER PUBLICATIONS

C. A. Thomas, Jr., et al., "A miniature microelectrode array to monitor the bioelectric activity of cultured cells," Exptl. Cell Res., vol. 74, No. 1, pp. 61-66, 1972.

D. T. O'Keeffe, et al., "Stimulus artifact removal using a software-based two-stage peak detection algorithm," J. Neurosci. Meth., vol. 109, No. 2, pp. 137-145, Aug. 2001.

J. W. Gnadt, et al., "Spectral cancellation of microstimulation artifact for simultaneous neural recording In Situ," IEEE Trans. Biomed. Eng., vol. 50, No. 10, pp. 1129-1135.

D. A. Wagenaar, et al., "Real-time multi-channel stimulus artifact suppression by local curve fitting," J. Neurosci. Meth., vol. 120, No. 2, pp. 17-24, Oct. 2002.

Y. Jimbo, et al., "A system for MEA-based multisite stimulation," IEEE Trans. Biomed. Eng., vol. 50, No. 2, pp. 241-248, Feb. 2003.

\* cited by examiner

CIRCUITS AND METHODS FOR ARTIFACT ELIMINATION

STATEMENT REGARDING FEDERALLY SPONSORED RESEARCH OR DEVELOPMENT

This invention was made in part with government support under Grant Number 1 ROI EB00786-01 awarded by the National Institutes of Health. Therefore, the government may have certain rights in this invention.

BACKGROUND

The present invention relates generally to systems and methods for acquiring signals through electronic devices in the presence of confounding signals that saturate the acquisition mechanism. More particularly, the present invention relates to electrodes that are used to both generate a signal in media and record the resulting signals from the media in order to identify a response of interest. The present invention is specifically well-suited to acquire electrical signals from biological tissues and cells after an electrical stimulation signal has been applied to the same or adjacent electrodes.

There are multiple instances in which sensors are saturated by their own signals. In the case of sonar, the minimum measurable distance is related to the residual ringing of transducers after stimulation. In the case of radar, amplifiers connected to antennas can be saturated due to resonant elements or multiple nearby targets. In the case of optical diodes there will be residual charge left in the junction that would alter the diode characteristics until discharged. In the case of electrodes, amplifiers will be saturated by residual charge remaining after applying a stimulus.

The common factor in all these cases is that a signal of considerable magnitude must be applied to the transduction element (that either acts both as a signal source and as a sensor or is part of a group of sensing elements in close proximity), while the signal to be measured is of a much smaller magnitude. Such large magnitude applied signals may be necessary to generate measurable responses or to achieve a desired range as signals rapidly decay with distance.

In the specific case of neural tissues hundreds of millivolts are required to achieve a response through extracellular electrodes, while the same electrodes will show signals in the tens of microvolts when the tissues generate a signal. This four-order-of-magnitude signal disparity, and its remaining effects on the electrode, will make signal recovery impossible unless a recovery technique, as the one presented herein, is used. Such interference is commonly referred to as an 'artifact', a term that includes the saturation of the signal amplifying elements and its effects in the signal processing chain, as well as the remaining disturbances that are present during the signal chain recovery period. The distinction between saturation and its after effects is made, because it is desired to completely eliminate or considerably reduce the saturation period, during which there is no possibility of recovering a signal. Other techniques may be used to further reduce artifacts once the signal chain is out of saturation.

The ability to measure direct responses from stimulated elements, and thus to record signals that were previously obscured by using those elements as a source, would enhance or enable use of closed loop control techniques in which the input and output of the system, biological or otherwise, share common elements. Techniques such as those of U.S. Pat. Nos. 20,050,282,149 and 6,114,164 can be enhanced by using the techniques herein described.

Literature and commercial systems present methods for stimulation and recording without interference from stimulation artifacts, usually at the expense of functionality. In the simplest method, an experimenter must designate electrodes as stimulation or recording sites for the duration of the experiment, thus sidestepping the problem of recording at the site of the largest artifacts. Often, electronics designers place sample and hold (S/H) circuitry at the input of the recording amplifier to prevent saturation of the electronic system during stimulation (see J. L. Novak and B. C. Wheeler, "Multisite hippocampal slice recording and stimulation using a 32 element microelectrode array," *J. Neurosci. Meth.*, vol. 23, no. 2, pp. 239-247, March 1988, and C. A. Thomas, Jr., P. A. Springer, G. E. Loeb, Y. Berwald-Netter, and L. M. Okun, "A miniature microelectrode array to monitor the bioelectric activity of cultured cells," *Exptl. Cell Res.*, vol. 74, no. 1, pp. 61-66, 1972).

Another common technique is to blank, or disable, recording amplifiers near stimulation sites for 100 ms or more after stimulation (see D. T. O'Keeffe, G. M. Lyons, A. E. Donnelly, and C. A. Byrne, "Stimulus artifact removal using a software-based two-stage peak detection algorithm," *J. Neurosci. Meth.*, vol. 109, no. 2, pp. 137-145, August 2001). Many techniques focus on post-processing to filter out stimulation artifacts from neighboring electrodes (see J. W. Gnadt, S. D. Echols, A. Yildirim, H. Zhang, and K. Paul, "Spectral cancellation of microstimulation artifact for simultaneous neural recording In Situ," *IEEE Trans. Biomed. Eng.*, vol. 50, no. 10, pp. 1129-1135, October 2003, D. A. Wagenaar and S. M. Potter, "Real-time multi-channel stimulus artifact suppression by local curve fitting," *J. Neurosci. Meth.*, vol. 120, no. 2, pp. 17-24, October 2002, and US Patent Application 20050277844 of Strother et al.) or the same electrode (U.S. Pat. No. 7,089,049 of Kerver et al.).

These approaches all concede the data closest to the stimulation, both temporally and spatially, as lost to the stimulation artifact. However, these data may represent the most significant response to the stimulation.

An alternative approach for reducing interference from stimulation artifacts is to return the stimulation electrode to its pre-stimulation voltage immediately after stimulation through an open-loop circuit (see Y. Jimbo, N. Kasai, K. Torimitsu, T. Tateno, and H. Robinson, "A system for MEA-based multisite stimulation," *IEEE Trans. Biomed. Eng.*, vol. 50, no. 2, pp. 241-248, February 2003). This approach provides stimulation while reducing the artifact, both at neighboring electrodes and at the stimulation electrode. However, a difficulty with this system is that, should neuronal activity or noise occur immediately before the start of a stimulation pulse, the sample and hold circuit would store a voltage that does not correspond to the actual electrode offset.

The approach described herein is different as it makes the measuring element itself part of the compensation system, and by using feedback to return the measuring system to a useful range, can compensate for effects that an open-loop system cannot. The technique described herein can be combined with existing signal processing techniques such as those discussed in the above paragraphs to further improve the recovery speed.

Accordingly, there is a need, and it would advance the state-of-the-art, to have apparatus and methods for acquiring signals from electronic devices in the presence of confounding signals that saturate the acquisition mechanism. There is also a need for improved stimulation and recording apparatus and methods for use with electrodes that are used to generate a signal in media and record the resulting signals from the media in order to identify a response of interest. There is also a need, and it would advance the state-of-the-art, to have apparatus and methods for use in acquiring electrical signals from biological tissues and cells that reduces or eliminates artifacts in order to identify a response of interest, and that may be advantageously embodied in an integrated circuit.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Figure 1:
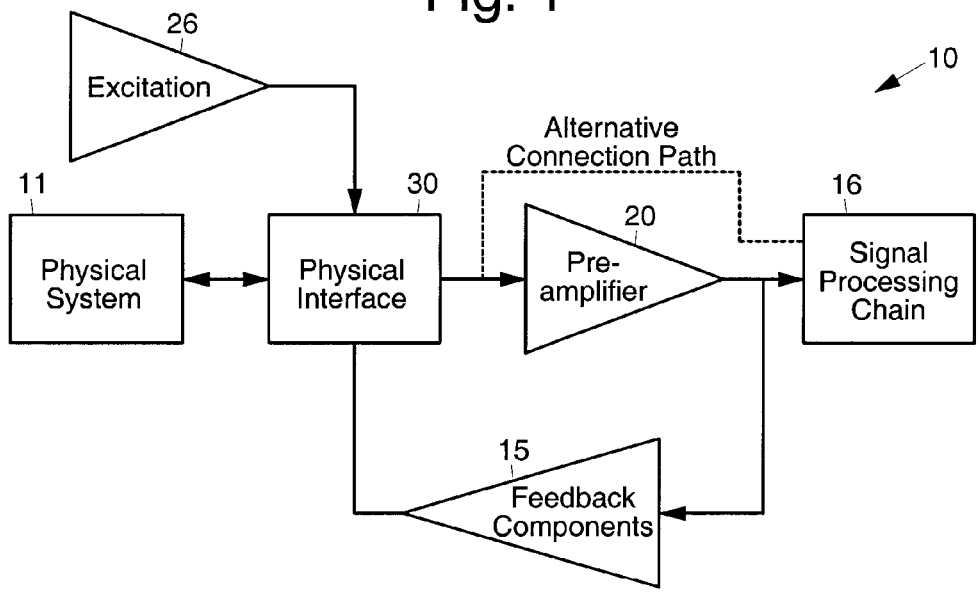
FIG. 1 illustrates an exemplary signal processing topology that generically illustrates operation of an exemplary technique for eliminating artifacts.

Referring to the drawing figures, disclosed are exemplary systems 10 (FIG. 1), circuits 10 (FIGS. 3, 6) and methods for acquiring signals through electronic devices in the presence of confounding signals that saturate the acquisition mechanism. More particularly, the present invention relates to electrodes that are used to both generate a signal in media and record the resulting signals from the media in order to identify a response of interest. The systems 10, circuits 10 and methods may be advantageously used with transducers, optical diodes, and electrodes, for example, to reduce or eliminate artifacts in order to identify a response of interest. The systems 10, circuits 10 and methods may be used to acquire electrical signals from biological tissues and cells, or other specimens, for example. Exemplary biological specimens include in vitro neural cultures, in vitro neural tissue slices, in vivo neural tissue, and in vitro osteoblasts. The systems 10, circuits 10 and methods may be embodied in an integrated circuit. The systems 10 and circuits 10 may generally be referred to as an artifact elimination system 10.

FIG. 1 illustrates an exemplary signal processing system 10 that illustrates implementation of an exemplary technique for eliminating artifacts. The exemplary signal processing system 10 comprises a physical system 11, such as a tissue specimen, for example. A physical interface 30 is provided, such as an electrode 30, for example, that interfaces to the physical system 11. A circuit 26 for exciting or stimulating the physical system 11 is coupled to the physical interface 30. The physical interface 30 is coupled to a preamplifier 20, which refers to initial elements of the circuitry necessary for the extraction of signals from the physical interface 30, whose output is coupled by way of a feedback mechanism 15 (feedback components 15) back to the physical interface 30. In the electronics art the term preamplifier most commonly refers to an amplifier with bandwidth, noise, and interfacing characteristics that take into account the specifics of the signal and the physical interface 30. The output of the preamplifier 20 is coupled to a signal processing chain 16 which comprises elements for the processing, storing, analysis, transmission, or display of signals for example. The signal processing chain 16 alone or in conjunction with preamplifier 20 may generally be referred to as the recording path, as it is the path that the signal follows from the physical system 11 to its final use. The use of a recording path that does not include the signal emanating from the specific preamplifier 20 but connects a signal processing chain 16 directly to the physical interface 30 is included under this disclosure. The use of a recording path comprising a signal processing chain 16 that uses a separate physical interface to obtain a signal from the physical system 11 is included under this disclosure. Furthermore, the preamplifier 20 and the feedback mechanism 15 remove confounding signals, independent of an excitation source.

Operation of the system 10 and artifact elimination technique is as follows. An excitation signal, such as a voltage or current pulse, RF pulse, or sinusoidal burst, is applied to the physical interface 30 (such as an electrode 30) during which direct recording from it is normally impossible and the recording path is blanked, or turned off, to avoid additional distortion. In most cases the preamplifier 20 will include storage elements that are required for or consequential to the application, the use of the same elements to provide the required memory for the recovery of the pre-excitation condition of the physical interface 30 is convenient as it reduces design requirements, but additional elements can be used without detriment to this disclosure. As soon as the stimulating signal is removed from the physical interface 30 (electrode 30), the preamplifier 20 is activated (the signal processing chain 16 can remain blanked during the recovery period to further reduce remaining artifacts) and the feedback mechanism 15 is activated, which forces a return of the recording path to its functional range by modifying conditions (electrode charge for example) of the physical interface 30. The feedback mechanism 15 may be continuously adapted to changes in the recording path, or made to follow a specific time profile, to further reduce remaining artifacts. Once the physical interface 30 has been brought into a desirable range, the feedback mechanism 15 is turned off and the rest of the recording path is reactivated. The preamplifier 20 characteristics can be modified during or after the activation of the feedback mechanism 15 to improve artifact performance. By directly affecting the measuring element (physical interface 30) this technique can be applied both directly to the recording path or in parallel to it with a separate artifact elimination path. In both cases the same results, albeit with different tradeoffs, occur. This procedure, when applied to electrodes 30, for example, can reduce the saturation time of the electronics by two orders of magnitude or more and make any remaining artifacts easier to manage.

Figure 3:
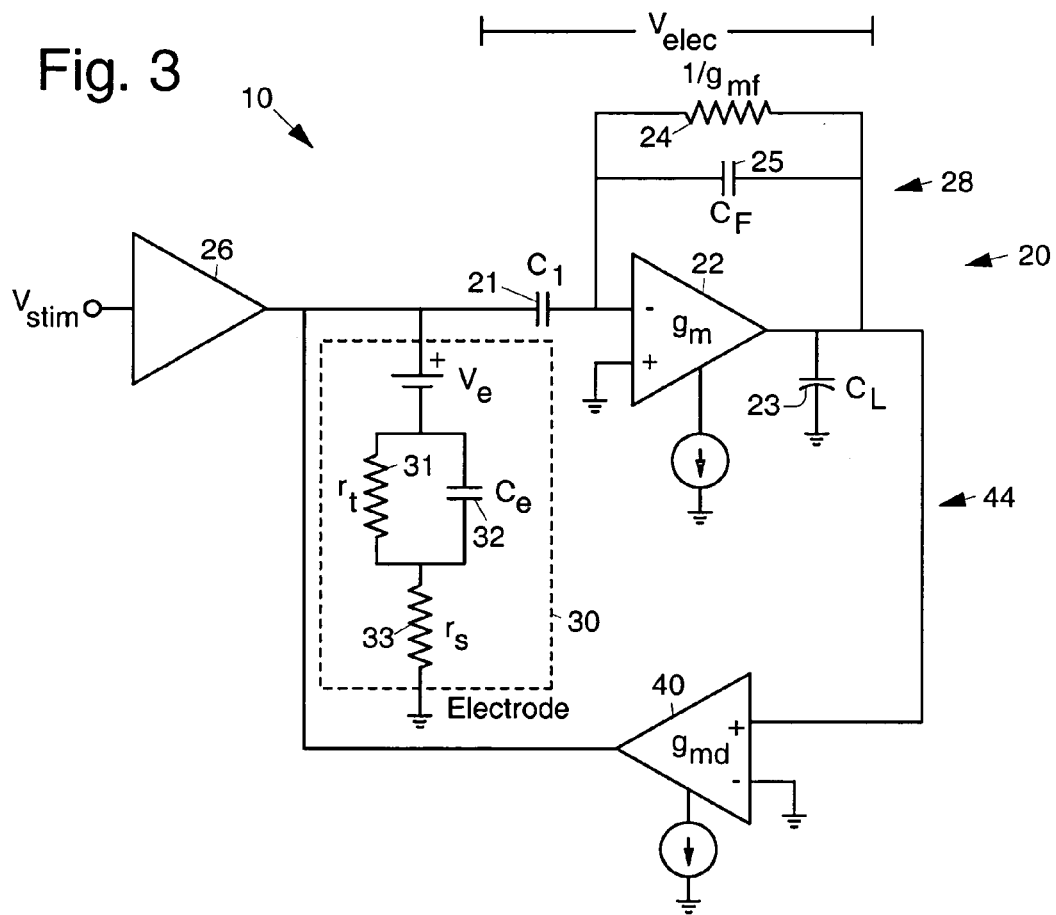
FIG. 3 illustrates an exemplary system-level circuit implementation for artifact elimination, showing a feedback loop including a discharge amplifier, electrode, and recording amplifier.
Figure 6:
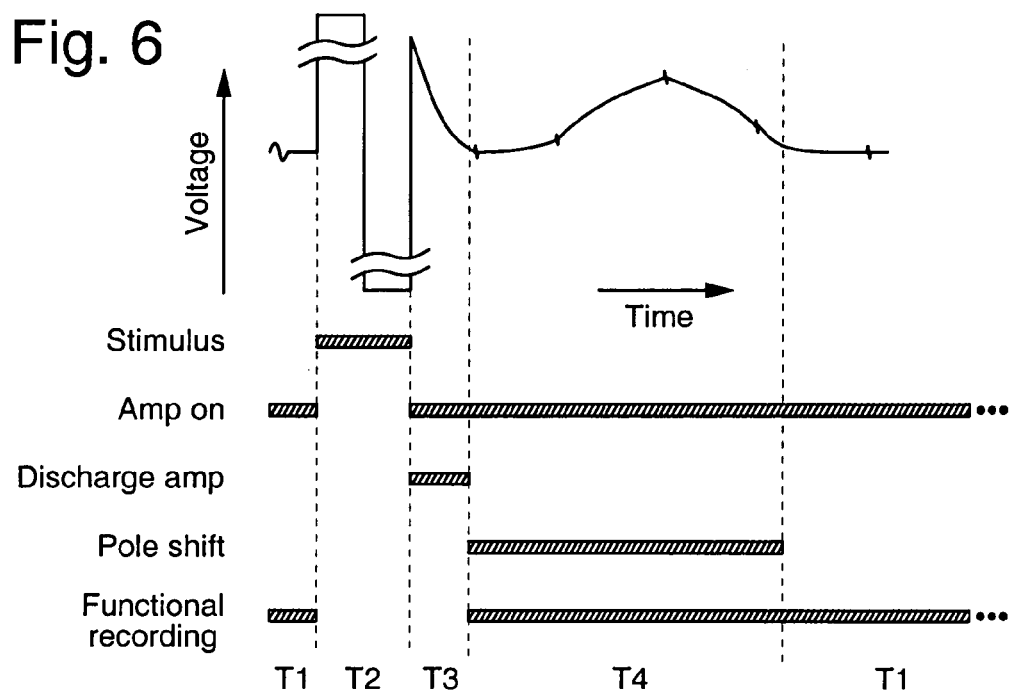
FIG. 6 shows an exemplary timing diagram that depicts sequential activation of different elements shown in FIGS. 3 and 5.

The specifics of the feedback mechanism 15 depend upon the frequency range of the signals of interest and of the recording electronics and on the variables of the physical interface 30 to be altered by it. An important consideration for the operation of the system 10 is the stability of the feedback mechanism 15 in the presence of and with possible variations of the physical interface 30. The specific implementations illustrated in FIGS. 3 and 6 is applied to electrodes, but it can be equally applied to light emitting and detecting diodes or ultrasonic transducers, but stability considerations and bandwidth limitations for the different components would change depending on the physical interface 30 and signal range of interest. The disclosed specific embodiment has been designed and optimized to be used for stimulating and recording signals from biological tissue through metal electrodes, and more specifically electrically active biological tissue including neural tissue, muscle fibers, pancreatic islet cells, osteoblasts, and the like, and may be used both for in vivo and in vitro applications.

Figure 2:
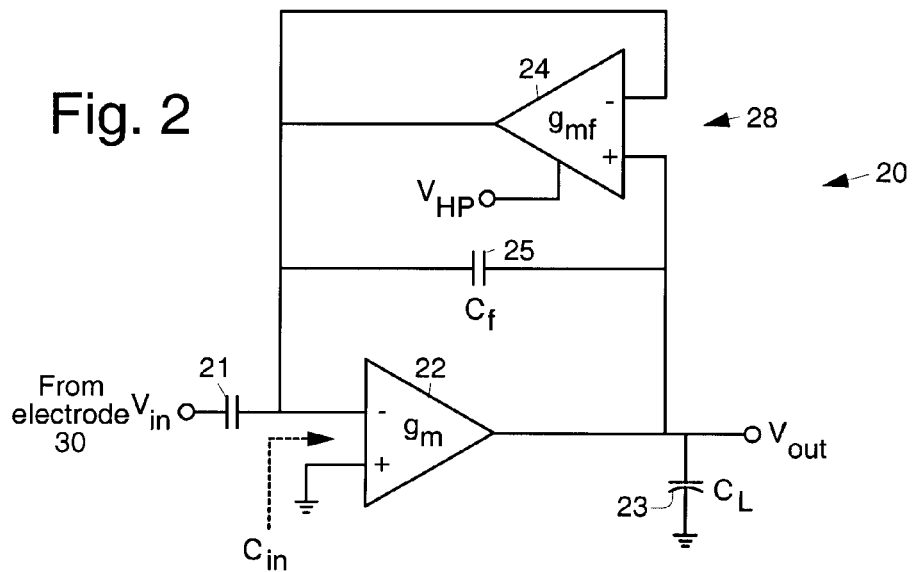
FIG. 2 illustrates an exemplary recording amplifier topology, including a feedback amplifier that tracks and stores electrode offsets.

FIG. 2 illustrates an exemplary recording preamplifier 20 that forms the core of the artifact elimination system 10. The exemplary recording preamplifier 20 comprises an input node ($V_{in}$) that is AC coupled through a capacitor 21 to a negative input of a recording amplifier 22. The positive input of the recording amplifier 22 is coupled to ground. An output of the recording amplifier 22 provides a voltage output of the recording preamplifier 20, which is coupled by way of a second capacitor 23 to ground. A feedback loop 28 around the recording amplifier 22 includes a feedback amplifier 24 and one or more feedback capacitors 25, in the electronics community both capacitors 21 and 25 are generally referred to as feedback capacitors. A positive input of the feedback amplifier 24 is coupled to the output of the recording amplifier 22. A negative input of the feedback amplifier 24 is coupled around the feedback amplifier 24 to its output and to the negative input of the recording amplifier 22.

To eliminate the interference with recording after stimulation, commonly referred to as a stimulation artifact, the electrode 30 is discharged back to its electrochemical offset voltage. This requires storage elements to keep track of the electrode offset voltage. The feedback capacitors 25, 21 and feedback amplifier 24 of the recording preamplifier 20 provide the storage elements necessary to track the average electrode voltage. By tracking the average voltage, rather than instantaneous voltage, interference from neuronal activity that occurs immediately before stimulation of the stored voltage is minimized. This topology also serves to AC couple the recording preamplifier 20, preventing offsets (including slowly drifting offsets) from interfering with recording.

FIG. 3 illustrates an exemplary system-level circuit implementation of the artifact elimination system 10 that provides for artifact elimination. FIG. 3 illustrates an exemplary topology of a discharge feedback loop 44 that performs artifact elimination. More particularly, FIG. 3 illustrates an exemplary discharge feedback loop 44 including a discharge amplifier 40, electrode 30, and recording preamplifier 20.

A stimulus or excitation voltage is input by way of an input stimulation or excitation amplifier 26, which applies the stimulus voltage to the electrode 30 and to the negative input of the recording amplifier 22. The idealized relevant physical characteristics of electrode 30 are represented by a model consisting of first and second series-connected resistors 31, 33 that are coupled to ground, and a capacitor 32 coupled in parallel with the first resistor 31. The feedback loop 28 around the recording amplifier 22 includes a feedback amplifier 24 (represented by a resistor) and one or more feedback capacitors 25, 21. The discharge amplifier 40 is coupled in a feedback path 44 (discharge feedback loop 44) around the recording amplifier 22 and electrode 30.

The exemplary artifact elimination system 10 shown in FIG. 3 thus comprises excitation circuitry 26 (the stimulation amplifier 26) that applies a current or voltage to an electrode 30 to electrically stimulate a specimen, such as a biological specimen, and signal acquisition circuitry (including the recording preamplifier 20 and discharge amplifier 40) that actively eliminates interference arising from the stimulation. The feedback capacitors 21, 25, and feedback amplifier 24 of recording preamplifier 20 is used as a storage element in a feedback loop 44 that incorporates the electrode 30. The discharge amplifier 40 provides a discharge path for the electrode 30.

In operation, after stimulation, the discharge amplifier 40 activates, providing a feedback element around the recording amplifier 20 and electrode 30, such that the feedback acts to drive the electrode 30 to its previous voltage. The discharge feedback loop 44 containing the discharge amplifier 40 and the recording preamplifier 20 acts to bring the output of the recording preamplifier 20 back to ground, and the stored voltage across the capacitors 21, 25 ensures that this corresponds to the electrode 30 returning to its previous voltage.

Figure 4:
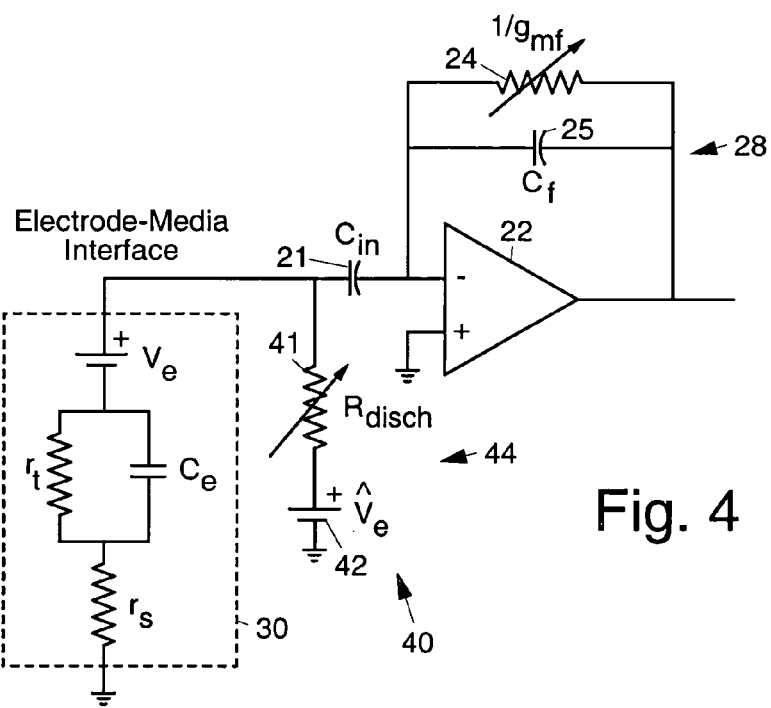
FIG. 4 illustrates an equivalent circuit of the circuit implementation shown in FIG. 2.

FIG. 4 illustrates an exemplary idealized model of the action of the discharge feedback loop 44. The discharge feedback loop 44 and discharge amplifier 40 are modeled as a conductive path to the electrode offset, as modeled by a variable resistor 41 (which is a function of the feedback loop 44 gain and the discharge amplifier 40 transconductance) and an offset voltage source 42 (due to the storage provided by preamplifier 20) in FIG. 4.

Figure 5:
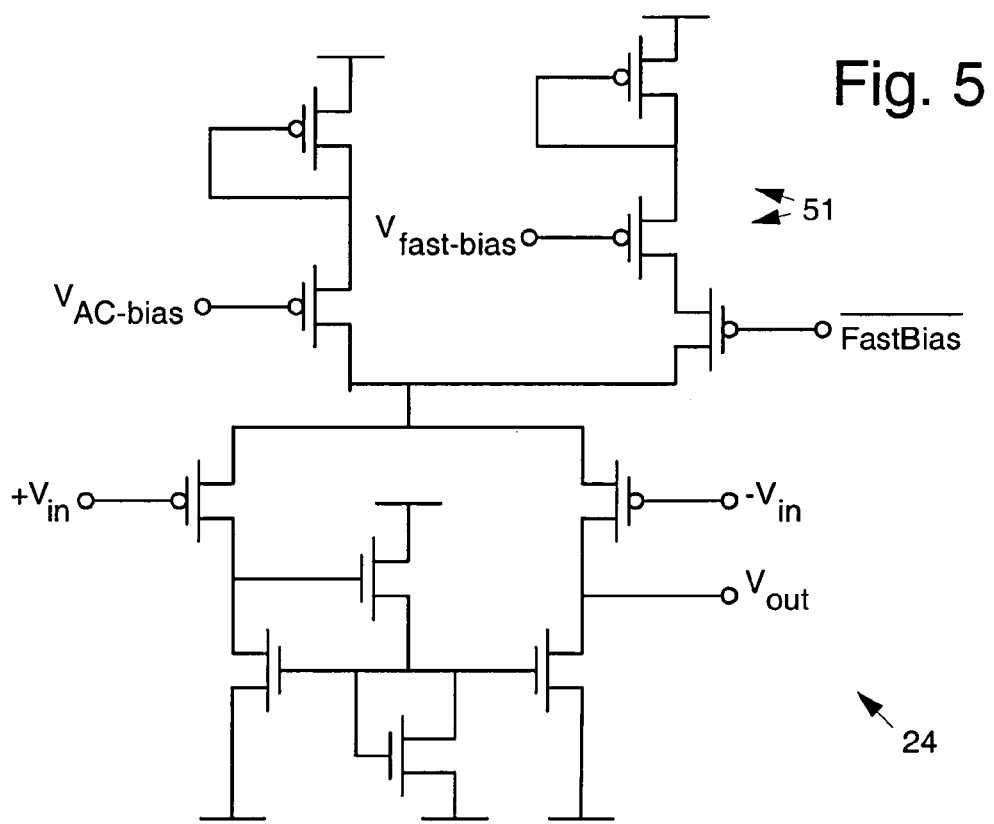
FIG. 5 illustrates an exemplary implementation of a feedback amplifier with a second tail current supply to improve transient signal rejection.

FIG. 5 illustrates a possible implementation of the feedback amplifier 24 shown in FIG. 2 that includes a modification to provide improved performance. AC coupling of the recording preamplifier 20 (provided by capacitor 21 and feedback amplifier 24) would continuously adapt out the offsets present in the system which can also serve to null out any artifacts remaining after activation and deactivation of the discharge circuitry. By momentarily increasing the speed of the offset tracking circuitry, that is increasing the dominant high-pass pole of the preamplifier 20 (which accordingly we refer to as pole shifting), the recording preamplifier 20 will filter out most of the remaining offset. That speed is proportional to the bias current of the feedback amplifier 24. Increasing the tail current to the feedback amplifier 24 after activation and deactivation of the feedback pathway has the desired effect of reducing the remaining artifact. The use of a second switchable tail current supply 51 in the feedback amplifier 24 allows for selectively increasing the speed of the offset rejection at the stimulation amplifier 26 without the need for changing system-wide biases.

FIG. 6 shows an exemplary timing diagram that depicts sequential activation of different elements shown in FIGS. 3 and 5. As shown in time segment T1, signals can be recorded prior to the onset of excitation (electrical stimulation). During the application of the excitation, the preamplifier 20 is turned off as indicated by timing segment T2. Immediately following the application of the excitation/stimulus, the electrode 30 is returned to its pre-excitation/stimulus value by engaging the feedback components (discharge amp 40 and preamplifier 20) for a duration given by timing segment T3. Following the discharge time segment T3, the cut-off frequency of the high pass filter may be optionally and temporarily shifted (segment T4, pole shifting) to expedite the return of the signals to the pre-stimulus/target value. After either the pole shifting time segment T4 or discharge amplifier time segment T3, the system will be back into recording mode (time segment T1). Additional signal processing may be employed to extract further information from time segment T4 or to enable the reduction of the duration of time segment T3.

Using the circuit implementation of the artifact elimination system 10 shown in FIG. 3, the speed of discharge of the electrode 30 may be limited by the time constants of the electrode 30 (mostly given by capacitor 32 and resistor 33) which can possibly extend the length of the discharge. To further accelerate such discharge, certain circuit modifications may be needed. From the simplified equivalent circuit for the discharge scheme shown in FIG. 4, it can be seen that if a negative discharge resistance ($R_{disch}$) is implemented, the effects of $R_s$ are reduced. This considerably reduces the discharge time constant of the artifact elimination system 10, thus reducing discharge time beyond what would otherwise be possible.

Figure 7:
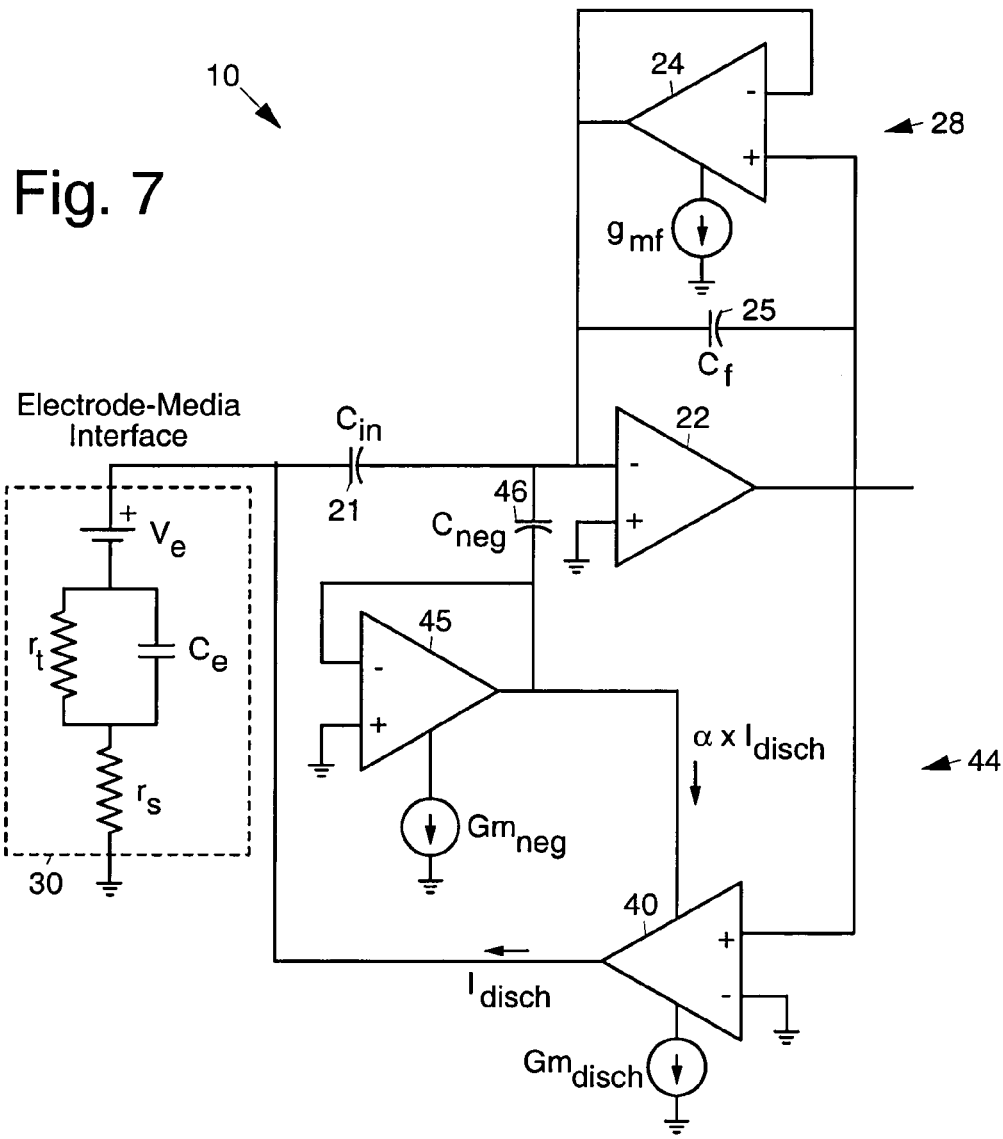
FIG. 7 illustrates an alternative exemplary embodiment of the circuit implementation shown in FIG. 3.

FIG. 7 illustrates an alternative exemplary embodiment of the artifact elimination system 10, introducing changes to the circuit of FIG. 3 to incorporate the aforementioned modification. The system shown in FIG. 7 may be used to generate a negative discharge resistance which specifically addresses the speed of removal of charge for electrodes 30, other circuit modifications can be used to address other types of physical interfaces 30.

A scaled copy of the discharge current from the discharge amplifier 40 is fed to a variable resistor 45 (implemented by an additional amplifier 45) providing positive feedback to the discharge loop 44 through an additional capacitor 46 ($C_{neg}$). Even though this circuit has the same equivalent representation given by FIG. 4, the presence of this positive feedback allows the discharge impedance 41 (which now is a function of capacitors 25, 21, and 46, the variable resistor 45, the transconductance of discharge amplifier 40, and the current copy fraction) to achieve negative values. By adjusting the discharge current and the positive feedback gain, it is possible to independently control the discharge time constant and the maximum discharge current, thus allowing for the optimization of stability and discharge speed. By adequately sizing the positive feedback components and currents feedback loop 44 stability and maximum discharge currents can be independently optimized.

Implantable neural stimulators or "brain pacemakers" have demonstrated great promise for relieving pain, reducing tremors, and treating depression. Currently available brain pacemakers operate blind to the stimulation environment and deliver constant, open-loop, electrical pulses to targeted areas of the brain. These programmable devices rely on patient feedback to optimize stimulus results and minimize side effects. However, patient feedback represents only a single measure of the device's performance. Simultaneous stimulation and recording allows the device to operate closed loop and quantitatively evaluate the tissue environment and stimulus response. The presently disclosed system 10 provides for new opportunities for implantable stimulators by imparting each implanted electrode 30 with multiple functions including near simultaneous stimulation and recording. Furthermore, the same circuit of FIGS. 3 and 6 can be directly recruited to carry out electrode impedance monitoring.

An example application of this technology is as follows. The recording system 10 monitors the brain for epileptic activity and upon detection, applies computationally derived stimuli and immediately (less than 4 ms) assesses the results. This strategy prevents a seizure before the patient is ever aware that it started. In effect, this translates the extraordinary results of Implantable Cardioverter Defibrillators (ICDs) to the neural environment.

Artifact elimination is required for any system where rapid switching between stimulation and recording is desired. This includes deep brain, spinal cord, and cardiac stimulators. The low operating power ensures extraordinary battery life and makes an integrated circuit chip implementation amenable to remote power harvesting strategies. The manufacturing of these chips may be outsourced to semiconductor foundries in high volumes at very low costs.

Eliminating the artifact, or residual charge that accumulates at an electrode-media interface, improves stimulation efficacy and safety and allows rapid switching between stimulating and recording functions. The residual charge that remains on the electrode after an applied stimulus, besides being potentially harmful to the electrode and tissues, easily saturates sensitive recording amplifiers and obscures cellular responses for up to half a second, an eternity in cellular time scales. For neural systems, stimulation signals are on the order of volts, while recorded signals are on the order of tens of micro-volts. Consequently, very small mismatches of 1% or less, which are common and acceptable in traditional circuit and signal processing designs, generate artifacts that saturate the signal acquisition chain in extracellular recordings. To fully eliminate the artifacts the remaining stimulation charge has to be dissipated to 1 part in 100,000 or more. Most existing designs attempt to cancel the artifact from the signal chain after it has been produced. The presently disclosed design eliminates the artifact from the source, the electrode 30 itself. As charge is being eliminated from the electrode 30 itself, an additional advantage of the described approach is the enabling of fast repetitive stimulation sequences without introducing long term saturation of the stimulation and surrounding electrodes. Thus the recovery time of surrounding electrodes is also improved. Additionally, by placing the electrode 30 in the discharge feedback loop 44, this design is able to compensate for nonlinearities and electrochemical effects. This strategy dramatically improves the post-stimulus time-to-recording and saves on computational complexity and power consumption.

The disclosed apparatus 10 may be advantageously employed in many types of systems and applications. For example, the apparatus 10 may be used with piezoelectric transducers, ultrasound (sonar) devices, optical diodes, and polarizable and non-polarizable electrodes (including glass, metallic, polymer, and composite), for example. The apparatus 10 may also be used in various biological applications including (vertebrate and invertebrate in vitro or in vivo) neural tissue, muscle fibers, pancreatic islet cells, osteoblasts, osteoclasts, some types of bacteria, algae, and plants, for example.

Figure 8:
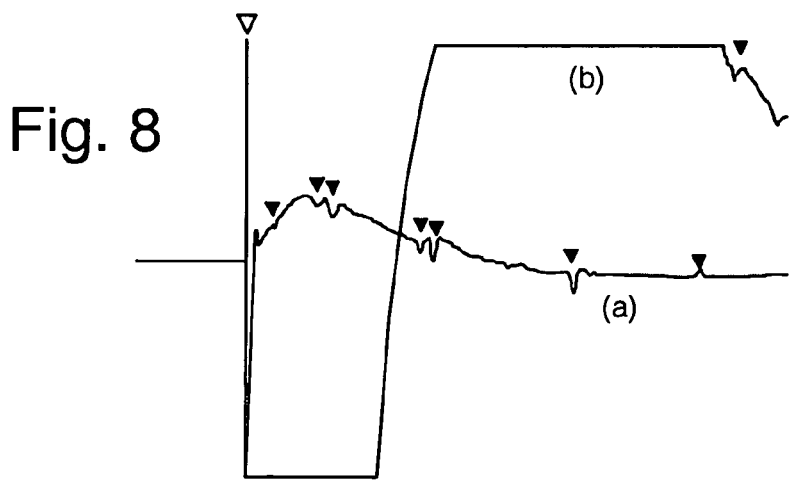
FIG. 8 is a graph that illustrates an exemplary demonstration of artifact elimination using the artifact elimination system.

FIG. 8 is a graph that illustrates an exemplary demonstration of artifact elimination using the disclosed artifact elimination system 10. The two traces in the graph shown in FIG. 8 represent recordings from the same electrode 30 both with (a) and without (b) the use of artifact elimination circuitry. Trace (a) shows neural signals recorded with the use of the circuitry contained in the artifact elimination system 10. Trace (b) shows neural signals recorded without the circuitry. Trace (b) quickly saturates, minimizing the ability to record useful neural signals. With active electrode discharge, the amplifiers are able to record neural signals (solid triangles) long before the system would recover on its own.

Thus, closed loop feedback systems and methods for acquiring electrical signals from biological tissues and cells that reduces or eliminates artifacts in order to identify a response of interest have been disclosed. It is to be understood that the above-described embodiments are merely illustrative of some of the many specific embodiments that represent applications of the principles discussed above. Clearly, numerous and other arrangements can be readily devised by those skilled in the art without departing from the scope of the invention.

What is claimed is:

1. Apparatus comprising:
   excitation circuitry that electrically excites a physical system by way of applying an excitation signal to a physical interface to the system; and
   signal acquisition circuitry that actively eliminates interference arising from the excitation signal, said signal acquisition circuitry comprises a recording amplifier in a discharge feedback loop that incorporates the physical interface, the discharge feedback loop further comprising a discharge amplifier configured to directly provide an electrical discharge path for the physical interface, wherein said discharge feedback loop eliminates interference arising from the excitation of the physical system by a continuous-time adjustment of an electrical characteristic of the physical interface toward a target state prior to a subsequent excitation signal being applied by the excitation circuitry, wherein said adjustment of the electrical characteristic is a function of a present condition and a pre-excitation condition of the physical interface.

2. The apparatus recited in claim 1 wherein the signal acquisition circuitry further comprises:
   an amplifier that is AC coupled to the physical interface.

3. The apparatus recited in claim 1 which is embodied in an integrated circuit.

4. A method for acquiring electrical signals from a physical system comprising:
   providing an excitation signal to the physical system by way of a physical interface to the system; and
   actively eliminating interference that arises from the excitation signal using signal acquisition circuitry coupled to the physical interface using a discharge feedback loop that comprises a recording amplifier, a discharge amplifier, and the physical interface, wherein the discharge amplifier is configured to directly provide an electrical discharge path for the physical interface, wherein said discharge feedback loop eliminates interference arising from the excitation of the physical system by a continuous-time adjustment of an electrical characteristic of the physical interface toward a target state prior to a subsequent excitation signal being applied by the excitation circuitry, wherein said adjustment of the electrical characteristic is a function of a present condition and a pre-excitation condition of the physical interface.

5. The method recited in claim 4 wherein the physical interface is selected from a group including piezoelectric transducers, ultrasound devices, optical diodes, polarizable and nonpolarizable electrodes.

6. The method recited in claim 4 wherein the physical system is selected from a group including vertebrate or invertebrate in vitro or in vivo neural tissue, muscle fibers, pancreatic islet cells, osteoblasts, and osteoclasts.

7. The method recited in claim 4 wherein the physical system is selected from a group including bacteria, algae, fungi, protists, and plants.

8. The method recited in claim 4 wherein the interference is actively eliminated by monitoring and discharging the physical interface to a value substantially equal to its pre-excitation conditions.

9. The method recited in claim 4 wherein the physical interface comprises an electrode, and wherein the interference is actively eliminated by tracking and storing an average electrode voltage and discharging the electrode voltage so that the physical interface is returned to its electrochemical offset voltage.

10. The method recited in claim 4 wherein actively eliminating interference reduces long term saturation induced by repetitive excitation.

11. Apparatus comprising:
    stimulation circuitry that electrically stimulates an in vitro or in vivo biological specimen by way of a physical interface to the biological specimen; and
    signal acquisition circuitry that actively eliminates interference using a discharge feedback loop that comprises a recording amplifier and a discharge amplifier, the discharge amplifier configured to directly provide an electrical discharge path for the physical interface, wherein said discharge feedback loop eliminates interference arising from the excitation of the biological specimen by a continuous-time adjustment of an electrical characteristic of the physical interface toward a target state, wherein said adjustment of the electrical characteristic is a function of a present condition and a pre-excitation condition of the physical interface.

12. The apparatus recited in claim 11 wherein the in vitro or in vivo biological specimen is selected from a group including vertebrate and invertebrate neural tissue, muscle fibers, pancreatic islet cells, osteoblasts, osteoclasts, bacteria, algae, fungi, protists, and plants.

13. The apparatus recited in claim 11 wherein the recording amplifier is coupled to the physical interface.

14. The apparatus recited in claim 11 which is incorporated into an implantable medical device.

15. A method for acquiring electrical signals from a biological specimen comprising:
    providing an electrical stimulus to the specimen via a physical interface; and
    actively eliminating interference that arises from the stimulation using a discharge feedback loop that comprises a recording amplifier and a discharge amplifier, the discharge amplifier configured to directly provide an electrical discharge path for the physical interface, wherein said discharge feedback loop eliminates interference arising from the electrical stimulus by a continuous-time adjustment of an electrical characteristic of the physical interface toward a target state prior to a subsequent electrical stimulus being applied by the circuitry that generates the electrical stimulus, wherein said adjustment of an electrical characteristic is a function of a present condition and a pre-excitation condition of the physical interface.

16. The method recited in claim 15 wherein the circuitry that generates the electrical stimulus electrically stimulates the biological specimen by way of an electrode.

17. The method recited in claim 15 wherein the in vitro or in vivo biological specimen is selected from a group including vertebrate and invertebrate neural tissue, muscle fibers, pancreatic islet cells, osteoblasts, osteoclasts, bacteria, algae, fungi, protists, and plants.

18. The method recited in claim 16 wherein the interference is actively eliminated by monitoring and discharging the electrode to a value substantially equal to its electrochemical offset voltage.

19. An apparatus comprising:
    circuitry that detects the presence of a confounding signal originating from an external excitation in a physical system by way of a physical interface to the system; and
    signal acquisition circuitry that actively eliminates the confounding signal, said signal acquisition circuitry comprises a recording amplifier in a discharge feedback loop incorporating the physical interface and a discharge amplifier, the discharge amplifier configured to directly provide an electrical discharge path for the physical interface, the discharge feedback loop configured to eliminate the confounding signal by a continuous-time adjustment of an electrical characteristic of the physical interface toward a target state prior to a subsequent excitation signal being applied by the excitation circuitry, wherein said adjustment of an electrical characteristic is a function of a present condition and a pre-excitation condition of the physical interface.

20. The apparatus recited in claim 19 wherein the signal acquisition circuitry further comprises:

an amplifier that is AC coupled to the physical interface.

21. The apparatus recited in claim 19 wherein the excitation circuitry is separate from the signal acquisition circuitry.

* * * * *